United States Patent [19]

Bluestein et al.

[11] 4,209,372

[45] Jun. 24, 1980

[54] ALKALINE AGAROSSE GEL ELECTROPHORESIS OF HEMOGLOBINS

[75] Inventors: Barry I. Bluestein, Lansing; Cyrus A. Lepp, Corning, both of N.Y.

[73] Assignee: Corning Glass Works, Corning, N.Y.

[21] Appl. No.: 44,462

[22] Filed: Jun. 1, 1979

[51] Int. Cl.² .................. G01N 33/16; G01N 27/26
[52] U.S. Cl. ................. 204/180 G; 23/230 B; 424/12
[58] Field of Search ............. 204/180 G, 299 R; 23/230 B; 424/12

[56] References Cited

U.S. PATENT DOCUMENTS

| | | | |
|---|---|---|---|
| Re. 24,752 | 12/1959 | Ressler | 204/180 G |
| 3,497,437 | 2/1970 | Louderback et al. | 204/180 G |
| 3,558,459 | 1/1971 | Granstrand et al. | 204/180 G |
| 3,607,695 | 9/1971 | Schneider | 204/180 G X |
| 3,692,654 | 9/1972 | Svendsen | 204/180 G X |

Primary Examiner—Arthur C. Prescott
Attorney, Agent, or Firm—William E. Maycock; Clinton S. Janes, Jr.

[57] ABSTRACT

The common hemoglobin variants A, $A_2$, F, S, and C are discretely separated by alkaline agarose gel electrophoresis employing (1) an agarose gel having a wet thickness of from about 0.1 to about 0.5 mm., (2) a gel buffer comprising tris(hydroxymethyl)aminomethane, ethylenediaminetetraacetic acid, and boric acid, and having an ionic strength of from about 0.065 to about 0.1 and a pH of from about 8.7 to about 9.1, (3) a well buffer comprising diethylbarbiturate and ethylenediaminetetraacetate and having an ionic strength of from about 0.01 to about 0.11 and a pH of from about 8.0 to about 9.5, and (4) a potential of from about 150 to about 300 volts.

20 Claims, No Drawings

ALKALINE AGAROSSE GEL ELECTROPHORESIS OF HEMOGLOBINS

BACKGROUND OF THE INVENTION

Interest in population-screening programs for abnormal hemoglobins in the United States has increased primarily because of the National Sickle Cell Disease Program developed by the Department of Health, Education and Welfare. Thus, screening for hemoglobinopathies has become very important within the past five years. For example, many hospitals now screen all incoming surgical patients for such abnormalities. Because electrophoresis on cellulose acetate is the primary procedure used in the Federal Sickle Cell Disease Program, cellulose acetate electrophoresis at pH 8.4–9.2 currently is the most common electrophoretic screening method for hemoglobinopathies. It has been found, however, that cellulose acetate cannot adequately separate certain combinations of hemoglobin variants. See for example, E. J. Hicks and B. J. Hughes, Clin. Chem., 21, 1072 (1975). Thus, in questionable cases, one must proceed to a secondary procedure such as electrophoresis on citrate agar to obtain a more definitive diagnosis.

The separation of hemoglobins A and F on an agar gel using a barbital buffer of pH 8.6 and ionic strength 0.03 has been reported, but at least one worker in the field questions the data, stating that at alkaline pH the separation of such two hemoglobins was impossible because of complex formation between the hemoglobins.

A hemoglobin screening system involving agarose gel electrophoresis currently is marketed by Corning Medical (Corning Glass Works, Medfield, Mass.), which separates hemoglobins at pH 8.6 by use of a discontinuous buffer system utilizing 2-amino-2-methyl-1-propanol. Such procedure, however, does not adequately resolve the common hemoglobin variants A, F, S and C.

Consequently, there still is a need for a rapid and simple electrophoretic procedure for the separation of the common hemoglobin variants.

SUMMARY OF THE INVENTION

Accordingly, the present invention provides, in a method for discretely separating the common hemoglobin variants A, $A_2$, F, S, and C by electrophoresis, the improvement which comprises employing:

A. an agarose gel having a wet thickness of from about 0.1 to about 0.5 mm.,

B. a gel buffer comprising tris(hydroxymethyl)aminomethane, ethylenediaminetetraacetic acid, and boric acid and having an ionic strength of from about 0.065 to about 0.1 and a pH of from about 8.7 to about 9.1, C. a well buffer comprising diethylbarbiturate and ethylenediaminetetraacetate and having an ionic strength of from about 0.01 to about 0.11 and a pH of from about 8.0 to about 9.5, and D. a potential of from about 150 to about 300 volts.

Thus, the method of the present invention is especially useful for the discrete separation of hemoglobins A, $A_2$, F, S, and C with a resolution which exceeds that of any cellulose acetate-based procedure presently available.

DETAILED DESCRIPTION OF THE INVENTION

The method of the present invention requires the use of an agarose gel having a wet thickness of from about 0.1 to about 0.5 mm. The nature of the agarose is not critical, provided that substantial amounts of agar or similar impurities are not present. Suitable agarose preparations are readily available commercially and have been found to be suitable in the method of the present invention. The amount of agar employed typically is about 1% weight per volume. It will be apparent to those having ordinary skill in the art that greater or lesser amounts of agarose can be employed, provided that appropriate adjustments in the other parameters are made.

Optionally, the gel can contain minor amounts, e.g. less than about 10% weight per volume, of one or more humectants. Examples of suitable humectants include sucrose, hydroxyethylcellulose, glycerine, sorbitol, and the like. A particularly useful amount of humectant is 5%, with sucrose being the preferred material. The humectant serves to aid in the retention of small amounts of water at the surface, thereby stabilizing the wet film. The humectant also serves as a dried film stabilizing agent. The use of a humectant such as sucrose is preferred.

In addition, the gel also can contain a small amount of a wetting agent which acts as a dried film stabilizing agent. The use of a wetting agent is, in practice, preferred. Typically, the wetting agent will be present in an amount less than about 0.1% weight per volume. The suitable wetting agents include anionic and nonionic surfactants, as well as other compounds having properties of a wetting agent. Examples of such compounds include, among others, polyvinyl alcohol, sulfate esters of alkyl phenoxy polyoxyalkylene alkanols, alkyl aryl sulfonates, alkali metal salts of the sulfates and sulfonates, fatty acid soaps, polyether alcohols, and the like. In addition to polyvinyl alcohol, specific examples of such wetting agents include, among others, nonyl phenyl polyoxyethylene sulfate, sodium lauryl sulfate, and nonyl phenyl polyoxyethylene ethanol. The preferred wetting agent is polyvinyl alcohol, provided that such material is essentially free of polyvinyl acetate.

The gel buffer comprises tris(hydroxymethyl)aminomethane, ethylenediaminetetraacetic acid, and boric acid. As already indicated, the gel buffer has an ionic strength of from about 0.065 to about 0.1 and a pH of from about 8.7 to about 9.1. Preferably, the ionic strength of the gel buffer is from about 0.075 to about 0.090, with an ionic strength of about 0.082 being most preferred. Preferably, the gel buffer pH is from about 8.8 to about 8.9. The most preferred ionic strength is conveniently obtained with a buffer which is about 0.06 M and consists essentially of 0.053 M tris(hydroxymethyl)aminomethane, 0.002 M ethylenediaminetetraacetic acid, and 0.0059 M boric acid. Obviously, the pH of the buffer, irrespective of the ratio of components, can be adjusted if necessary to the desired pH, provided that large adjustments are not required.

As already pointed out, the gel must have a thickness of from about 0.1 to about 0.5 mm. A particularly preferred wet thickness is from about 0.3 to about 0.4 mm. While the gel can be prepared by any known method, a most convenient means of gel preparation is the use of cassette-type molds, such as are disclosed in U.S. Pat. Nos. 3,449,265 and 3,635,808.

The well buffer comprises diethyl barbituarate and ethylenediaminetetraacetate and has an ionic strength of from about 0.01 to about 0.11 and a pH of from about 8.0 to about 9.5. As a practical matter, the well buffer is conveniently prepared from sodium diethylbarbiturate and sodium ethylenediaminetetraacetate, with the pH being adjusted as desired with aqueous hydrochloric acid. Preferably, the well buffer has an ionic strength of from about 0.04 to about 0.11, with an ionic strength of about 0.06 being most preferred. Preferably, the well buffer has a pH of from about 8.55 to about 8.65. In an especially preferred embodiment, the well buffer consists of 0.025 M sodium diethylbarbiturate and 0.017% weight per volume sodium ethylenediaminetetraacetate, with the pH of the resulting solution being adjusted to 8.6 with aqueous hydrochloric acid.

The electrophoresis is carried out in accordance with well known procedures, using a potential of from about 150 to about 300 volts. The preferred potential is from about 225 to about 270 volts, with about 250 volts being most preferred.

If desired, the amounts of hemoglobin variants thus separated can be estimated by visually inspecting the gel. Such amounts can be quantitated, however, by various known methods. For example, the gel can be scanned directly in a densitometer, taking advantage of the heme color in the variants. Alternatively, the variants can be visualized indirectly by staining the variants with a nonspecific protein stain such as amido black or Ponceau S, followed by scanning in a densitometer at an appropriate wavelength. Other methods, of course, will be readily apparent to those having ordinary skill in the art.

The method of the present invention is further illustrated, but not limited, by the example which follows. Unless otherwise specified, all temperatures are in °C.

MATERIALS AND METHODS

Gel Buffer. The gel buffer, having an ionic strength of about 0.082 and a pH of 8.86±0.05 at room temperature, was prepared by dissolving 6.44 g. of tris(hydroxymethyl)-aminomethane, 0.62 g. of ethylenediaminetetraacetic acid, and 0.4. g. of boric acid in 900 ml. of deionized glass-distilled water. The pH was checked and adjusted with saturated boric acid solution, and the volume adjusted to 1 liter.

Agarose. The gel solution was prepared by adding 1.0 g. of agarose (Seakem, Marine Colloids, Inc., Rockland, Maine), 5.0 g. of sucrose, and 15 mg. of polyvinyl alcohol (99% hydrolyzed, Matheson, Coleman and Bell) to 100 ml. of the gel buffer. The mixture was heated, with stirring, in a boiling water bath for 30 minutes after total dissolution of the components had occurred.

Preparation of Gel Films. Empty cassette molds were obtained from Corning Medical and used to form the thin gels. The gel solution was cooled to 65°-70° before being injected into the lower nipple of the mold with a glass syringe to which a piece of plastic tubing, 3 mm. in diameter, was attached. The mold was held in an upright position during injection to facilitate removal of air from the upper nipple. After injecting about 5 ml. of gel solution, the cassette mold was placed on a flat benchtop, and a flat weight of about 500 g. was placed on the mold to expel any excess gel. After the gel solution had set (about 5 minutes at ambient temperature), each gel was wrapped in stretch plastic and aluminum foil and stored at 4° for 24 hours before use. The gels thus prepared were stable for at least 6 months if kept tightly sealed.

Electrophoresis. Hemoglobin standards and samples were obtained as lyophilizates from Gelman Instrument Company or the Center for Disease Control, Atlanta, Ga., or as hemolysates from the Georgia Department of Human Resources, Atlanta, Ga. The apparatus employed was the Corning Medical electrophoresis cell connected by leads to a model 3-1155 regulated power supply (Buchler Instrument, Fort Lee, N.J.). Hemolysates were prepared according to the Corning Medical Electrophoresis Operations Procedures Manual; 1 $\mu$l. of hemolysate was applied to each cassette sample well.

Each well of the cell base was filled with 75 ml. of 4° running or well buffer consisting of, per liter of buffer, 5.15 g. of sodium diethylbarbiturate and 0.175 g. of sodium ethylenediaminetetraacetate. The pH of the buffer was adjusted to 8.6±0.05 with 2 M aqueous hydrochloric acid. Gels were placed in the gel holdercover and set into the cell base so that the gel edges were immersed in buffer. A constant potential of 250 volts was applied for 20 minutes.

Visualization. Gels were stained after separation by immersion in amido black stain for 5 minutes. The stain consisted of amido black 10B (Sigma Chemical Company, St. Louis, Mo.), 2.0 g., dissolved in dilute aqueous acetic acid (50 ml. of glacial acetic acid and 950 ml. of water). The gel then was rinsed in the dilute aqueous acetic acid and dried in a Corning Medical drying oven for 20 minutes. The dried gel was completely destained in the dilute aqueous acetic acid and rinsed in fresh destaining solution to completely remove background color.

Using a variety of hemoglobin AF samples supplied by the Georgia Department of Human Resources, the method described herein resulted in the discrete and complete separation of all samples into the appropriate bands, thereby completely separating hemoglobins, A, $A_2$, F, S, and C.

What is claimed is:

1. In a method for discretely separating the common hemoglobin variants A, $A_2$, F, S, and C by electrophoresis, the improvement which comprises employing:
   A. an agarose gel having a wet thickness of from about 0.1 to about 0.5 mm,
   B. a gel buffer comprising tris(hydroxymethyl)aminomethane, ethylenediaminetetraacetic acid, and boric acid, and having an ionic strength of from about 0.065 to about 0.1 and a pH of from about 8.7 to about 9.1,
   C. a well buffer comprising diethylbarbiturate and ethylenediaminetetraacetate and having an ionic strength of from about 0.01 to about 0.11 and a pH of from about 8.0 to about 9.5, and
   D. a potential of from about 150 to about 300 volts.

2. The method of claim 1 in which the gel wet thickness is from about 0.3 to about 0.4 mm.

3. The method of claim 1 in which the gel buffer has an ionic strength of from about 0.075 to about 0.090.

4. The method of claim 3 in which the gel buffer has an ionic strength of about 0.082.

5. The method of claim 4 in which the gel buffer has a pH of from about 8.8 to about 8.9.

6. The method of claim 5 in which the gel buffer is about 0.06 M consists essentially of 0.053 M tris(hydroxymethyl)aminomethane, 0.002 M ethylenediaminetetraacetic acid, and 0.0059 M boric acid.

7. The method of claim 1 in which the gel buffer has a pH of from about 8.8 to about 8.9.

8. The method of claim 1 in which the well buffer has an ionic strength of from about 0.04 to about 0.11.

9. The method of claim 8 in which the well buffer has an ionic strength of about 0.06.

10. The method of claim 9 in which the well buffer has a pH of from about 8.55 to about 8.65.

11. The method of claim 10 in which the well buffer is about 0.025 M and consists essentially of 0.025 M sodium diethylbarbiturate and about 0.017% weight per volume sodium ethylenediaminetetraacetate.

12. The method of claim 1 in which the well buffer has a pH of from about 8.5 to about 8.7.

13. The method of claim 1 in which the potential is from about 225 to about 270 volts.

14. The method of claim 1 in which the potential is about 250 volts.

15. The method of claim 1 in which the gel contains a humectant at a level of from 0 to about 10% weight per volume.

16. The method of claim 15 in which the humectant is sucrose.

17. The method of claim 16 in which the humectant is present at a level of about 5% weight per volume.

18. The method of claim 1 in which the gel contains a wetting agent at a level of from 0 to about 0.1% weight per volume.

19. The method of claim 18 in which the wetting agent is polyvinyl alcohol.

20. The method of claim 19 in which the wetting agent is present at a level of about 0.015% weight per volume.

* * * * *